(12) United States Patent
Mileham et al.

(10) Patent No.: US 8,171,803 B2
(45) Date of Patent: May 8, 2012

(54) AIR SAMPLING APPARATUS AND METHOD

(75) Inventors: Russell D. Mileham, Brookings, SD (US); George W. Schossow, White Bear Lake, MN (US)

(73) Assignee: Health Diagnostics Tools, LLC, Brookings, SD (US)

(*) Notice: Subject to any disclaimer, the term of this patent is extended or adjusted under 35 U.S.C. 154(b) by 264 days.

(21) Appl. No.: 12/392,884

(22) Filed: Feb. 25, 2009
(Under 37 CFR 1.47)

(65) Prior Publication Data
US 2009/0193911 A1 Aug. 6, 2009

Related U.S. Application Data

(60) Division of application No. 11/223,805, filed on Sep. 9, 2005, now Pat. No. 7,513,940, which is a continuation-in-part of application No. 11/101,193, filed on Apr. 7, 2005, now abandoned.

(51) Int. Cl.
*G01N 1/22* (2006.01)

(52) U.S. Cl. ................ 73/861.42; 73/863.02

(58) Field of Classification Search ............ 96/252, 96/253, 244, 272, 278, 329, 413; 95/149; 73/28.04, 28.05, 31.05, 861.42, 861.79, 863.02, 73/863.03, 864; 261/108–110, 112.1
See application file for complete search history.

(56) References Cited

U.S. PATENT DOCUMENTS

| | | | |
|---|---|---|---|
| 3,236,045 A | 2/1966 | Berger et al. | |
| 3,603,155 A | 9/1971 | Morris et al. | |
| 3,702,048 A * | 11/1972 | Howick | 96/272 |
| 3,881,898 A | 5/1975 | Darby et al. | |
| 3,921,456 A | 11/1975 | Newcomb, Jr. et al. | |
| 3,960,524 A * | 6/1976 | Cumpston, Jr. | 95/151 |
| 3,977,254 A | 8/1976 | Brouwer | |
| 4,005,999 A * | 2/1977 | Carlson | 95/221 |
| 4,067,705 A | 1/1978 | Kurz | |
| 4,172,865 A * | 10/1979 | Steier | 261/62 |
| 4,236,443 A | 12/1980 | Schossow | |
| 4,239,515 A * | 12/1980 | Yanagioka et al. | 96/272 |
| 4,401,444 A | 8/1983 | Teller | |
| 4,449,816 A | 5/1984 | Kohsaka et al. | |
| 4,868,398 A | 9/1989 | Mulcey et al. | |
| 4,942,135 A | 7/1990 | Zaromb | |
| 5,107,713 A | 4/1992 | Peck et al. | |
| 5,141,538 A * | 8/1992 | Derington et al. | 96/329 |
| 5,279,646 A | 1/1994 | Schwab | |
| 5,725,634 A | 3/1998 | Takasuga et al. | |
| 5,855,652 A | 1/1999 | Talley | |
| 5,861,316 A | 1/1999 | Cage et al. | |
| 5,967,332 A | 10/1999 | Willeke | |
| 6,059,865 A * | 5/2000 | Poteat | 96/236 |

(Continued)

OTHER PUBLICATIONS

"U.S. Appl. No. 11/223,805, Non-Final Office Action mailed Mar. 14, 2008", 11 pgs.

(Continued)

*Primary Examiner* — Frank Lawrence, Jr.
(74) *Attorney, Agent, or Firm* — MDIP LLC

(57) ABSTRACT

A sampling system includes a collection module including a gas handler, and a flow controller in communication with the gas handler of the collection module. The flow controller controls the gas handler to move a selected volume of gas through the collection module.

4 Claims, 6 Drawing Sheets

U.S. PATENT DOCUMENTS

| | | | |
|---|---|---|---|
| 6,267,016 | B1 | 7/2001 | Call et al. |
| 6,295,864 | B1 | 10/2001 | You et al. |
| 6,453,759 | B1 | 9/2002 | Lebski et al. |
| 6,546,812 | B2 | 4/2003 | Lewis |
| 6,741,056 | B1 | 5/2004 | Hall |
| 6,818,035 | B2 | 11/2004 | McGahey, Jr. |
| 7,722,708 | B2 * | 5/2010 | Powell et al. .................. 96/234 |
| 2003/0000189 | A1 | 1/2003 | Honda et al. |
| 2003/0167859 | A1 | 9/2003 | Dickson et al. |
| 2008/0017040 | A1 | 1/2008 | Mileham et al. |

OTHER PUBLICATIONS

"U.S. Appl. No. 11/223,805, Response filed Jun. 13, 2008 to Non-Final Office Action mailed Mar. 14, 2008", 16 pgs.

"U.S. Appl. No. 11/223,805, Final Office Action mailed Aug. 22, 2008", 9 pgs.

"U.S. Appl. No. 11/223,805, Response filed Oct. 22, 2008 to Final Office Action mailed Aug. 22, 2008", 12 pgs.

"U.S. Appl. No. 11/223,805, Notice of Allowance mailed Nov. 26, 2008", 6 pgs.

"BioCapture(r) 650 Air Sampler", MesoSystems Technology, Inc., Albuquerque, NM 87107, (published prior to Apr. 7, 2005), 1 pg.

"Sceptor Gets $15M Contract for U.S. Postal Service Work", *American City Business Journals*, http://web.archive.org/web/20040627235420/http://kansascity.bizjournals.com/kansascity/stories/2003/12/01/daily18.html, (archived Jun. 27, 2004), 2 pgs.

"Sceptor Hooks Up With N.Y. Firm to Develop Warning Systems", *The Business Journal*, http://web.archive.org/web/*/http://kansascity.bizjournals.com/kansascity/stories/2002/07/15/daily4.html, (archived Apr. 24, 2003), 1 pg.

"Spincon Aerosol Bio Sampler (DETBD24)", *Life Safety Systems, Inc.*, http://web.archive.org/web/20041110020258/http://www.lifesafetysys.com/osb/itemdetails.cfm/ID/555, (archived Nov. 10, 2004), 1 pg.

* cited by examiner

AIR SAMPLING APPARATUS AND METHOD

This application is a Divisional of U.S. application Ser. No. 11/223,805, filed Sep. 9, 2005, now U.S. Pat No. 7,513,940, which is a Continuation-in-Part of U.S. Application No. 11/101,193, filed Apr. 7, 2005, now abandoned, which are incorporated herein by reference.

FIELD OF THE INVENTION

The present invention is related to a system for obtaining air samples. More specifically, the present invention relates to methods and apparatus for sampling air that is portable and which operates under control of a microprocessor.

BACKGROUND OF THE INVENTION

There are many specific situations where there is a pressing need to know of the presence of a chemical agent or a virus or the like. The presence of specific chemical agents must be monitored inside and outside of factories that use hazardous materials. There are also instances where diseases can spread through a herd of animals and early detection through monitoring can be used to contain a disease. Still another instance is the intentional introduction of a disease or harmful chemical into a large population. Yet another need is for military troops when involved in a conflict where an enemy is not beyond employing chemical warfare in a conflict.

Agriculture is the largest economic sector in the United States. Of that sector, the value of livestock and poultry is approximately $100 billion dollars. Protecting U.S. livestock from disease is a top priority, not only because of the economic losses to the producer when diseases occur, but also the economic losses incurred by all related industries, including the food industry. However, the intensification of the livestock industry has allowed the majority of the livestock to be raised on fewer and larger farms, resulting in increased vulnerability to widespread disease transmission. These disease outbreaks lead to a loss of livestock productivity through the death of the animal, reduced yield, or reduced reproductive ability. Some livestock diseases are also transmissible to humans. For these reasons, disease prevention or early detection is critical to minimize the production losses and the associated economic losses.

Vaccination and antibiotic treatment are in widespread use in the United States; however these practices cannot prevent all disease occurrences. When disease outbreaks occur, it is essential that the disease be diagnosed at the earliest possible detection time to prevent or minimize production losses.

Aside from natural disease transmission, agricultural bioterrorism is a large security concern for Homeland Defense. The intentional introduction of diseases such as Foot and Mouth disease could spread rapidly on-farm and from farm to farm via aerosol transmission. Affected areas would be forced to destroy all animals, which would have an enormous economic impact on the producer and the economy of the surrounding area. Although an act of agricultural bioterrorism may not be an immediate threat to the general public, the fear and unease generated by such an attack could also have an impact on the national economy.

The emerging threat of exposure to toxicants in chemical weapons, and toxic industrial chemicals (TICs) is also a major concern for large populations. While the threat of chemical weapons is self evident, that of TICs may be less obvious. However, since TICs are easier to obtain than traditional warfare agents, terrorists are most likely to release TICs in a chemical attack. TICs are also a concern for civilian populations near chemical plants and industries that use them in daily processes, such as paper mills, waste management facilities and plastic manufacturers.

There is currently a wide range of instruments available for measuring chemical agents and TICs. These instruments use many different technologies including solid-state chemical sensors, calorimetric chemical sensors, sensor arrays, and analytical techniques such as photo ionization detection and gas chromatography. These instruments range in price from $10 to many tens of thousands of dollars. The primary disadvantage of many of these instruments is that they are designed to measure the quantity of a specific chemical rather than a broad range of toxic chemicals. This means that many different instruments are needed to evaluate a potential emergency, which results in large equipment costs. The use of the current invention may allow a single general purpose analytical instrument, such as a mass spectrometer, to be used to test air samples for a broad range of chemical agents and TICs.

BRIEF DESCRIPTION OF THE DRAWINGS

The invention is pointed out with particularity in the appended claims. However, a more complete understanding of the present invention may be derived by referring to the detailed description when considered in connection with the figures, wherein like reference numbers refer to similar items throughout the figures, and:

The description set out herein illustrates the various embodiments of the invention, and such description is not intended to be construed as limiting in any manner.

DETAILED DESCRIPTION

In the following detailed description of the preferred embodiments, reference is made to the accompanying drawings that form a part hereof, and in which are shown by way of illustration specific embodiments in which the invention can be practiced. The embodiments illustrated are described in sufficient detail to enable those skilled in the art to practice the teachings disclosed herein. Other embodiments can be utilized and derived therefrom, such that structural and logical substitutions and changes can be made without departing from the scope of present inventions. The following detailed description, therefore, is not to be taken in a limiting sense, and the scope of various embodiments of the invention is defined only by the appended claims, along with the full range of equivalents to which such claims are entitled.

Figure 1:
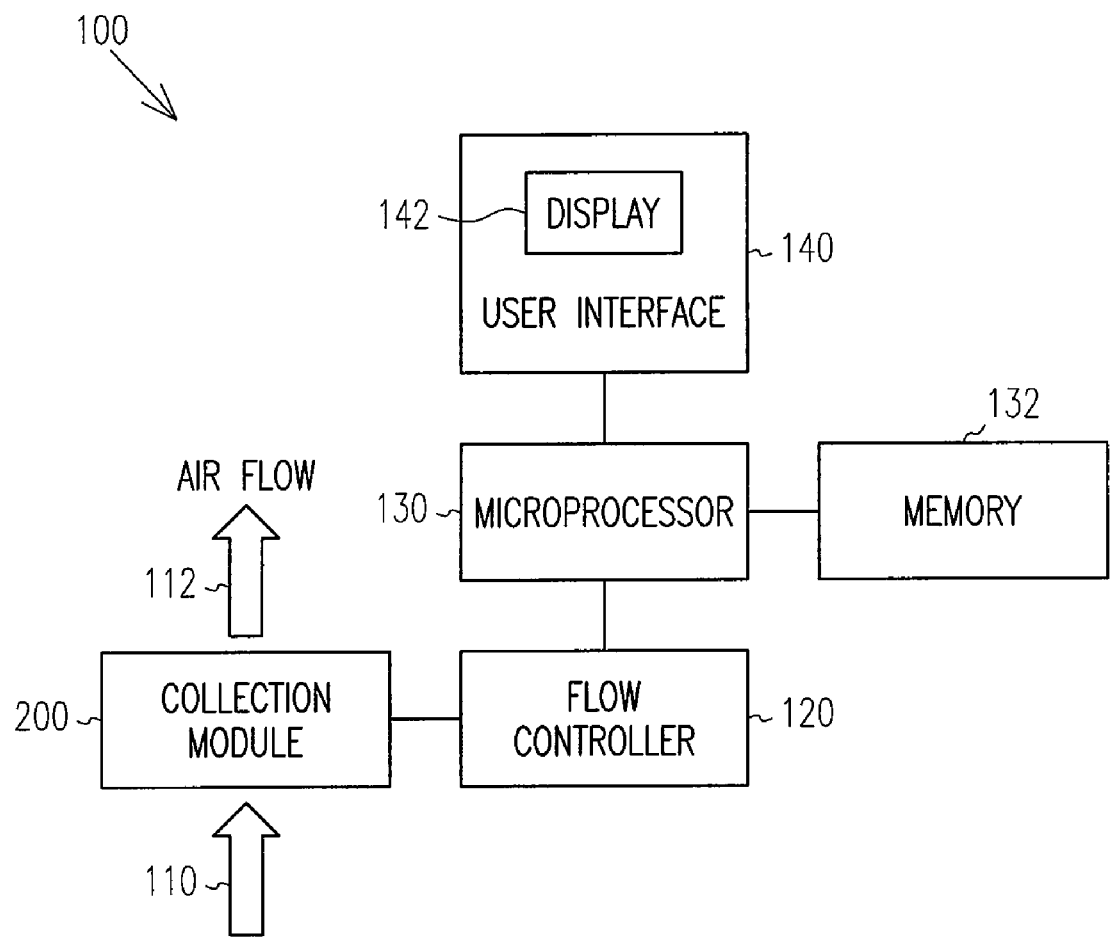
FIG. 1 is a schematic view of an air sampling system, according to an example embodiment.

FIG. 1 is a schematic view of an air sampling system 100 according to an exampled embodiment. The air sampling system 100 includes a collection module 200. Air is moved through the collection module 200, and sampled for substances within the air or gas moved through the collection module 200. Movement of the air through the collection module 200 is depicted by a first air flow arrow 110 representing an intake to the collection module 200 and the air flow arrow 112 which represents an exhaust port for the air flow from the collection module 200. The collection module 200 is in communication with a flow controller 120. The flow controller is in communication with a microprocessor 130. The microprocessor 130 can be a microprocessor associated with a personal computer or can be a dedicated microcontroller geared toward specific tasks. The microprocessor 130 is also in communication with a user interface 140. The microprocessor 130 also includes access to a memory module 132. The memory module 132 can be any sort of memory, such a disk drive, solid state memory, a memory stick, or the like. The user interface 140 can be any type of user interface including a numeric display or a cathode ray tube type display. A display 142, as shown in FIG. 1, is part of the user interface 140 in this particular example embodiment.

Figure 2:
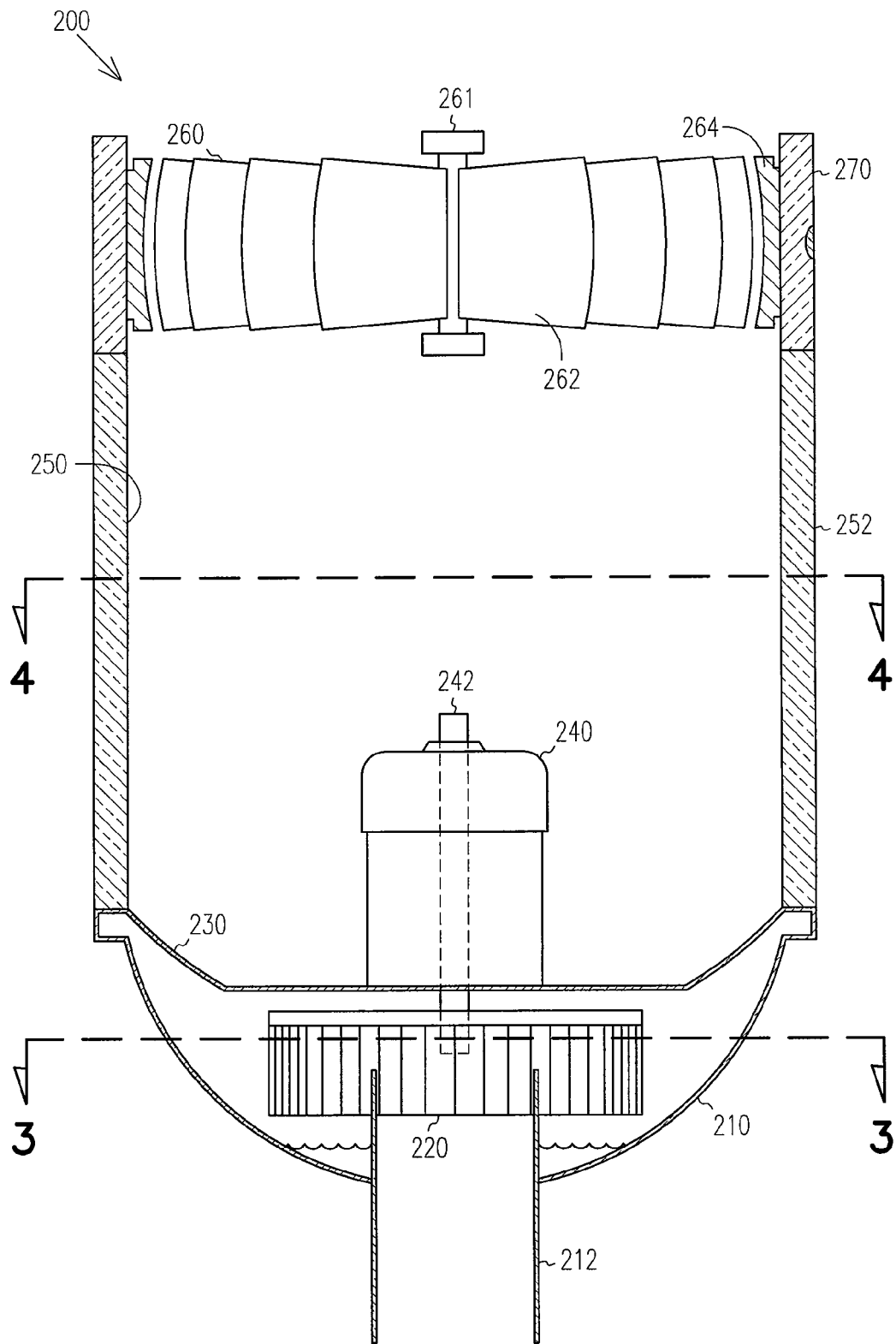
FIG. 2 is a schematic view of a collection module for an air sampling system, according to an example embodiment.

FIG. 2 is a schematic view of a collection module 200 for an air sampling system, according to an example embodiment. The collection module 200 includes a collection bowl 210 and an air inlet 212. The collection bowl 210 is concave in shape. The air inlet or inlet 212 is tubular and sealed with respect to the collection bowl 210 so that liquid solvents can be held within the collection bowl 210. A liquid solvent can be any type of solvent, such as de-ionized water, phosphate buffer solution, or any solvent formulated to dissolve TICs or preserve biological agents. The solvent is also referred to as a collection buffer and is held at the bottom of the bowl around the inlet 212. The inlet is tubular and extends above the bottom of the collection bowl 210. The inlet terminates between the top and bottom of the collection bowl 210. Therefore, the inlet 212 forms a dam which prevents the outflow of the collection buffer or solvent from the collection bowl 212. Placed around the inlet and within the bowl is a fan 220. The fan 220 is a squirrel cage rotary type fan in this particular example embodiment. The fan is positioned so that it rotates about the inlet 212 and specifically about the terminating portion of the inlet within the collection bowl 210. The rotating fan 220 pulls air or another gas sample through the inlet 212 and then directs the air toward the walls of the collection bowl 210. The fan 220 also moves the collection buffer or solvent up the sidewalls from the bottom of the collection bowl. As a result the fan moves both the gas or air as well as the collection buffer or solvent to an upper portion of the walls of the collection bowl 210. When the air or other gas strikes the solvent, portions of the air are dissolved within the solvent. When the fan 220 is turned off, the collection buffer or solvent moves back to the bottom of the collection bowl 210 and includes certain substances from the air that is sampled or that passed through the collection module 200.

Attached to the collection bowl is a frame 230. As shown in FIG. 2, the frame 230 is attached to the upper lip of the collection bowl 210. Attached to the frame is a motor 240, such as an electric motor. The electric motor includes a shaft 242. The fan 220 is attached to the motor shaft 242. The frame 230 has openings therein which allow air pulled into the inlet 212 to pass into an exhaust area 250 of the collection module 200. The exhaust portion 250 of the collection module 200 includes a sidewall 252. The sidewall 252 is also attached to the lip of the collection bowl 210. Attached to the sidewall 252 of the exhaust portion 250 is an impeller, or vane anemometer 260. The impeller or vane anemometer 260 is driven by the volume or an amount of gas being exhausted through the exhaust portion 250 of the collection module 200. For a particular given cross-section of the exhaust portion 250, an amount or volume of gas passing through the exhaust portion 250 can be determined based upon the number of rotations of the impeller or the number of revolutions per minute of the impeller for a given amount of time. The vane anemometer, or impeller, includes an impeller 262 on a shaft 261. At least one tip of a blade of the impeller 262 is magnetized or carries a magnet, as depicted by reference numeral 264. Also attached to the sidewall 252 of the exhaust portion 250 is a Hall effect sensor 270. As the magnetized portion 264 of the impeller 262 passes the Hall effect sensor 270, a signal is induced in the Hall effect sensor 270 indicating that a revolution or portion of a revolution has occurred. For example, if only one blade tip on the impeller 262 is magnetized 264, then each time the Hall effect sensor produces a signal, it represents one revolution of the impeller blade. On the other hand, if two blade tips of the impeller are magnetized or carry magnets, then for each two signals from the Hall effect sensor 270, one revolution is recorded. Knowing the number of revolutions of the impeller or knowing the number of revolutions per minute of the impeller 262 for a selected amount of time allows a determination of the amount of gas exhausted through the exhaust portion 250 of the collection module 200. Thus, a sample of a selected size can be passed through the collection module 200 to allow for a determination of a concentration of a substance within a selected volume of gas passed through the collection module 200.

Figure 3:
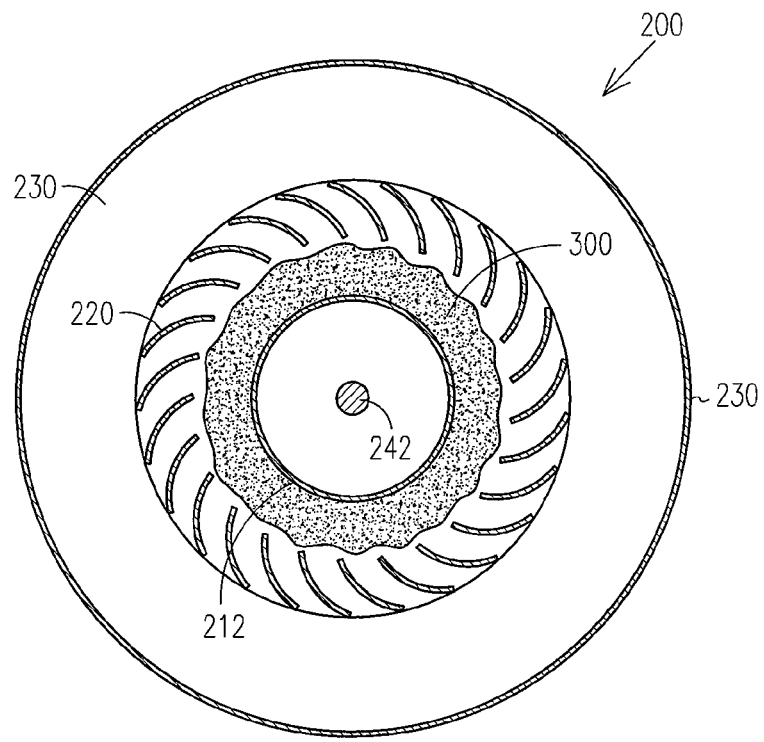
FIG. 3 is a cross-sectional schematic view of a collection module for an air sampling system along line 3-3 of FIG. 2, according to an example embodiment.

FIG. 3 is a cross-sectional schematic view of a collection module 200 for an air sampling system along line 3-3 of FIG. 2. As shown in FIG. 3, the fan 220 is positioned about the circumference of the tubular inlet 212. The fan 220 rotates on shaft 242. The fan 220 is positioned within the collection bowl 210, along with a solvent or collection buffer 300. The collection buffer or solvent 300 is within the bowl but outside the inlet 212. It should be noted that the inlet 212 is shown as a tubular, or circular, inlet and that other inlets having different cross-sectional shapes can also be used. As shown in FIG. 3, the fan 220 is not being rotated since the collection buffer or solvent 300 is positioned near the tubular inlet 212.

Figure 4:
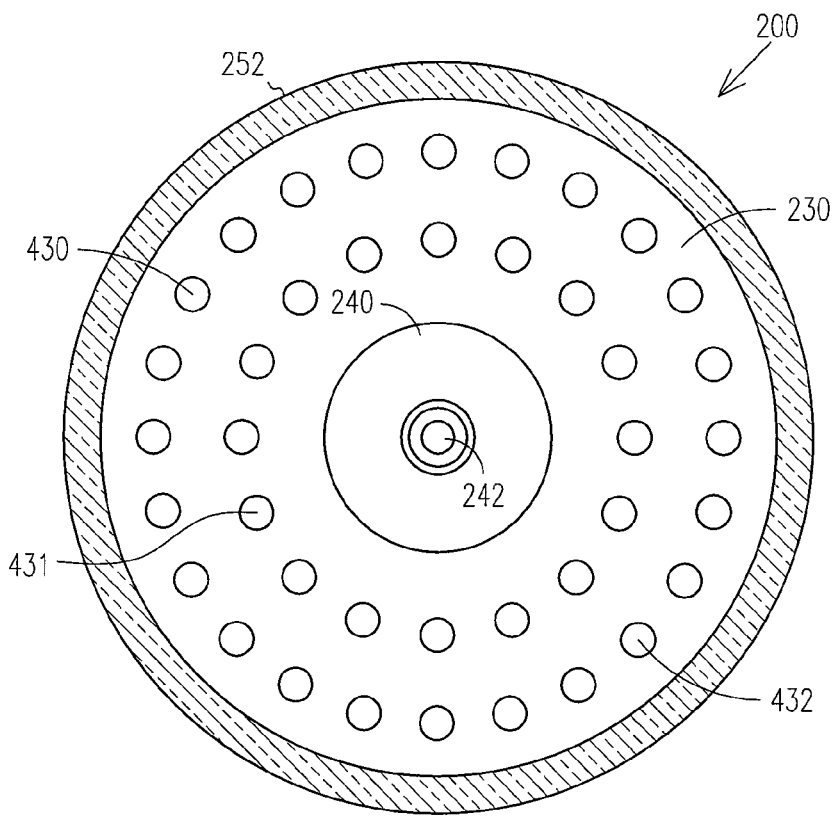
FIG. 4 is a cross-sectional schematic view of a collection module for an air sampling system along line 4-4 of FIG. 2, according to an example embodiment.

FIG. 4 is a cross-sectional schematic view of a collection module 200 for an air sampling system along line 4-4 of FIG. 2. As shown in FIG. 4, the collection module 200 includes a frame 230 that includes a plurality of openings, such as openings 430, 431, 432. The openings allow the air or gas to pass through the frame to the exhaust portion 250 (shown in FIG. 2) of the collection module 200. The motor 240 is attached to the frame 230. The motor 230 rotates the motor shaft 242 to which the fan 220 is attached (shown in FIGS. 2 and 3). The cross sectional view also shows the sidewall 252 of the exhaust portion of the collection module 200. The motor is connected to the flow controller 120 and the microprocessor 130 (see FIG. 1). The flow controller 120 and the microprocessor 130 control the motor and more specifically the volume of a sample of air or other gas that flows through the collection module 200.

Figure 5:
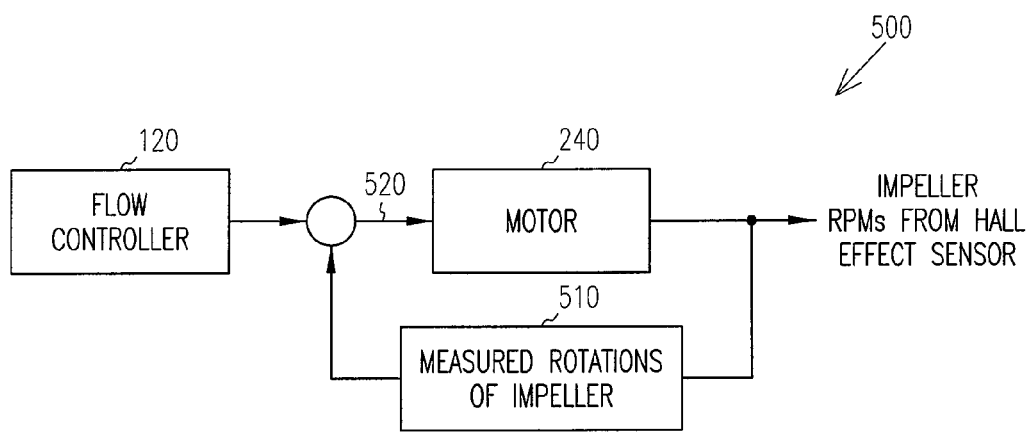
FIG. 5 is a schematic view of a feedback control used in the flow controller of an air sampling system, according to an example embodiment.

FIG. 5 is a block diagram showing a feedback control system 500 for the collector module 200, according to an example embodiment. The feedback control system 500 can be used to control the fan 220 for a selected number of rotations. The feedback control system 500 can also be used to control the speed of the motor 240 of the fan 220 so that a selected amount of gas, such as air, is sampled. The flow controller 120 inputs a target value for the number of turns of the impeller 262 of the vane anemometer 260. The impeller rotations or rotations per minute are measured using the Hall effect sensor 270 (shown in FIG. 2). Knowing the number of turns of the impeller 262 as well as the cross section of the exhaust portion 250 of the collection module 200 is correlated to the volume of gas or air passing through the collection module. Once the selected number of turns of the impeller 262 are achieved, the flow controller 120 stops the motor 240. It also may be necessary to control the speed of the motor 240 to assure that an appropriate sample is collected. In this case, the speed of the impeller 262 is measured and fed back to the flow controller 120. If the speed is too fast or too slow, the flow controller 120 produces a control signal 520 to the motor 240 to either speed up or slow down the motor 240 to which the fan 220 is attached. Once the number of turns or the length of time associated with a sample size is achieved, the motor 240 is shut down, the collection buffer or solvent 300 is removed from the collection bowl 210 and analyzed.

Figure 6:
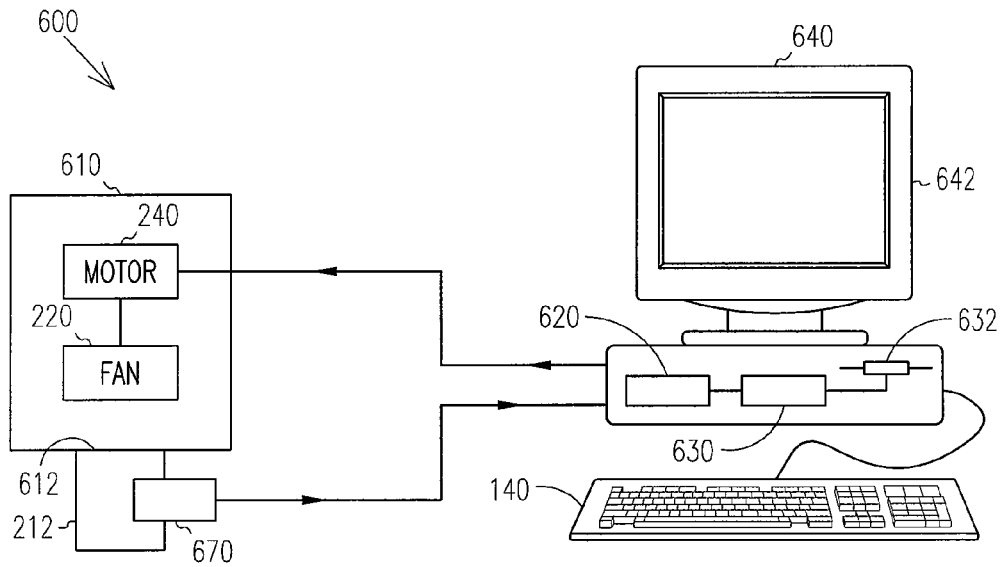
FIG. 6 is a schematic view of an air sampling system that includes a collection module that is controlled, in part, by a pressure differential sensor, according to an example embodiment.

FIG. 6 is a schematic view of an air sampling system 600 that includes a collection module 610 that is controlled in part by a differential pressure sensor 670, according to an example embodiment. The collection module 610 includes a motor 240, a motor shaft 242, and a fan 220 attached to the motor shaft 242. The collection module 610 also includes an air inlet 212. The air inlet has an end 612 proximate the fan 220. The collection module 610 also includes many of the same features of the collection module shown in FIG. 2. For example, the fan 220 is positioned near the end 612 of the inlet 212. Movement of the fan moves a solvent up from the bottom of the collection bowl and on to the sidewalls of the collection bowl and also moves air or another gas through the inlet 212. The air sampling system 600 also includes a personal computer 640 that includes a display 642, a microprocessor 630, memory attached to the microprocessor 632, as well as a flow controller 620. The personal computer 640 also includes a user interface 140, such as a keyboard. FIG. 6 shows that in addition to a microprocessor 630 being merely a microcontroller or a microprocessor, the functions can also be done or the microprocessor can be provided by a personal computer 640. A differential pressure sensor 670 is positioned in the air inlet 212. The differential pressure sensor 670 measures a pressure difference between the air inlet 212 and the exterior of the air sampling system 600. If a pressure differential is maintained for a certain length of time, then the size of the sample or the volume of air passing through the collection module 610 can be determined. The differential pressure sensor 670 is part of a feedback control loop. The reading from the differential pressure sensor 670 can be fed back to the flow controller 620 and the microprocessor 630 to determine if the motor 240 is turning too fast or too slow. The flow controller 620 can then be used to vary the speed of the motor 240 to produce the differential pressure sensor value required for a specific amount of time to produce a volume of air or sample size.

Figure 7:
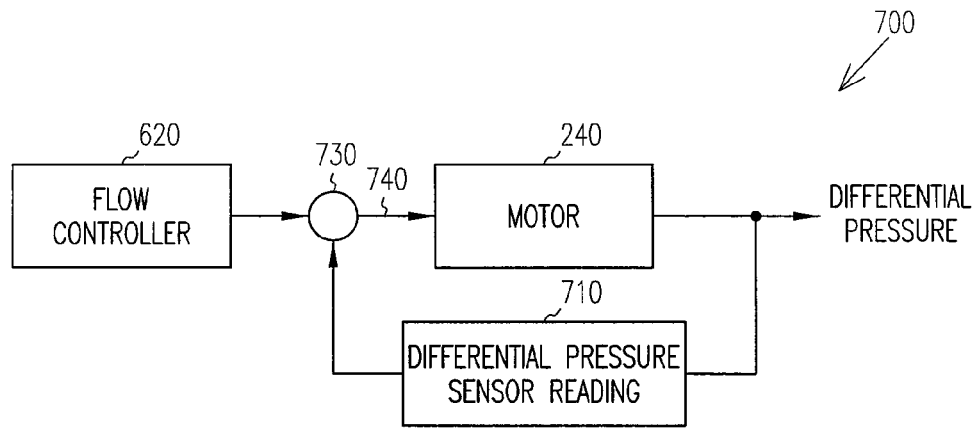
FIG. 7 is a schematic view of a feedback control used in the flow controller of an air sampling system, according to an example embodiment.

FIG. 7 is a block diagram showing a feedback control system 700 for the collector module 200, according to an example embodiment. The feedback control system 700 is used to control the motor 240 and the attached fan 220 for a selected period of time. Specifically, the feedback control system 700 control the speed of the motor 240 and the attached fan 220 so that a selected pressure differential is maintained over a selected sampling time. The flow controller 620 inputs a target value for the pressure differential 720. The motor 240 and attached fan 220 are rotated which produces a pressure differential. The pressure differential is sensed and read and a signal 710 of the actual pressure differential is produced and input to a comparator 730. The comparator 730 compares the target value for the pressure differential 720 to the signal of the actual pressure differential 710 and produces a control signal 740 to the motor 240. The control signal 740 speeds up the motor 240 if the actual pressure differential signal is less than the target pressure differential. The control signal 740B slows the motor 240 if the actual pressure differential signal is more than the target pressure differential. The control signal 740 maintains the speed of the motor 240 if the actual pressure differential signal is substantially equal to the target pressure differential. The pressure differential is controlled to maintain a substantially constant pressure differential for a selected amount of time. After the selected amount of time, the flow controller 620 shuts down the motor 240. Knowing the pressure differential and the diameter of the inlet 212 (see FIG. 6), the sample size of the air or gas volume can be determined. Once the volume of gas for the sample size is passed through collection module 600, the motor 240 is shut down, the collection buffer or solvent 300 (see FIG. 3) is removed from the collection bowl and analyzed.

Figure 8A:
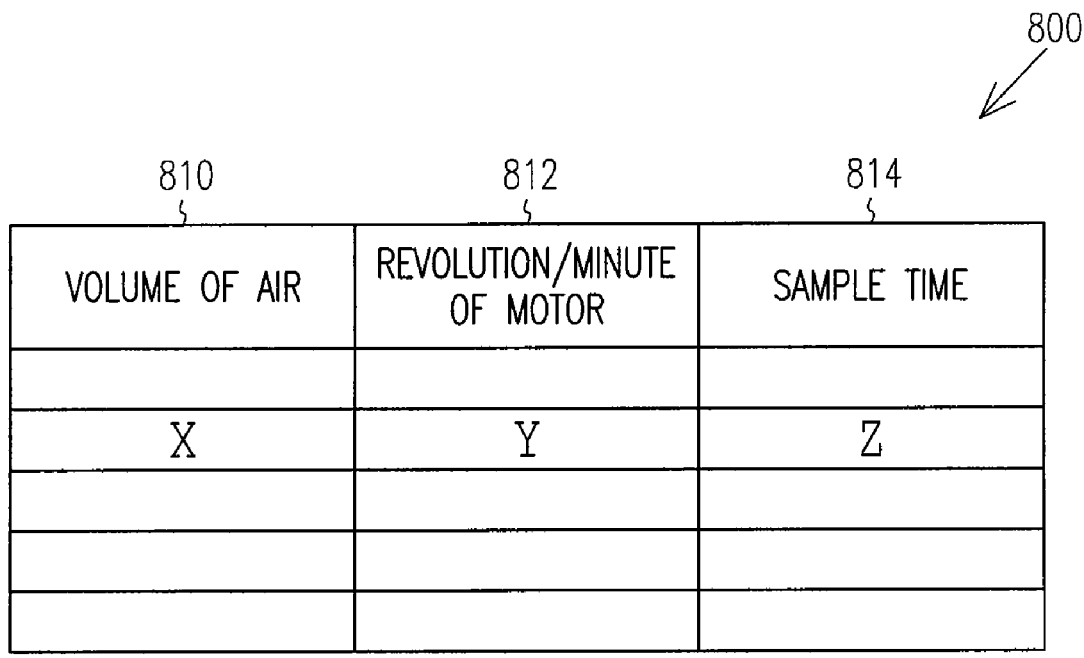
FIG. 8A illustrates a look up table for use in controlling the motor of a collection module, according to an example embodiment.

FIG. 8A illustrates a lookup table 800 for use in controlling the motor 240 of a collection module, such as collection module 200 or collection module 600, according to an example embodiment. The lookup table can be used to store an amount of air or volume of air 810, the number of revolutions per minute of the motor 812, and a sample time 814. The lookup table 800 is stored in the memory, such as memory 132 (shown in FIG. 1) of a microprocessor. The microprocessor 132 in the flow controller 120 have access to the memory 132 (shown in FIG. 1). The lookup table 800 can be useful in either a closed-loop type control feedback system or in an open-loop control system. FIG. 8A illustrates a lookup table for use in a feedback control loop. Using the lookup table 800, the motor and fan are rotated for a selected number of revolutions or at a selected number of revolutions per minute 812 for a selected sample time 814 to produce a volume of air 810. The number of revolutions are counted and fed back to determine whether a selected sample size or volume of an example has been achieved. The counted revolutions can be converted to revolutions per minute by dividing the number of counted revolutions by minutes. For example, using lookup table 800 the motor 240 would be spun at Y revolutions per minute 812 for a sample time of Z units of time to produce a volume of air X. The control associated with the collection module 200 (shown in FIG. 5) and the control system used to control the motor 240 in the collection module 610 (shown in FIG. 7) are both closed loop, feedback control systems. In an open-loop control system, there is no feedback from a sensor or other measurement device.

Figure 8B:
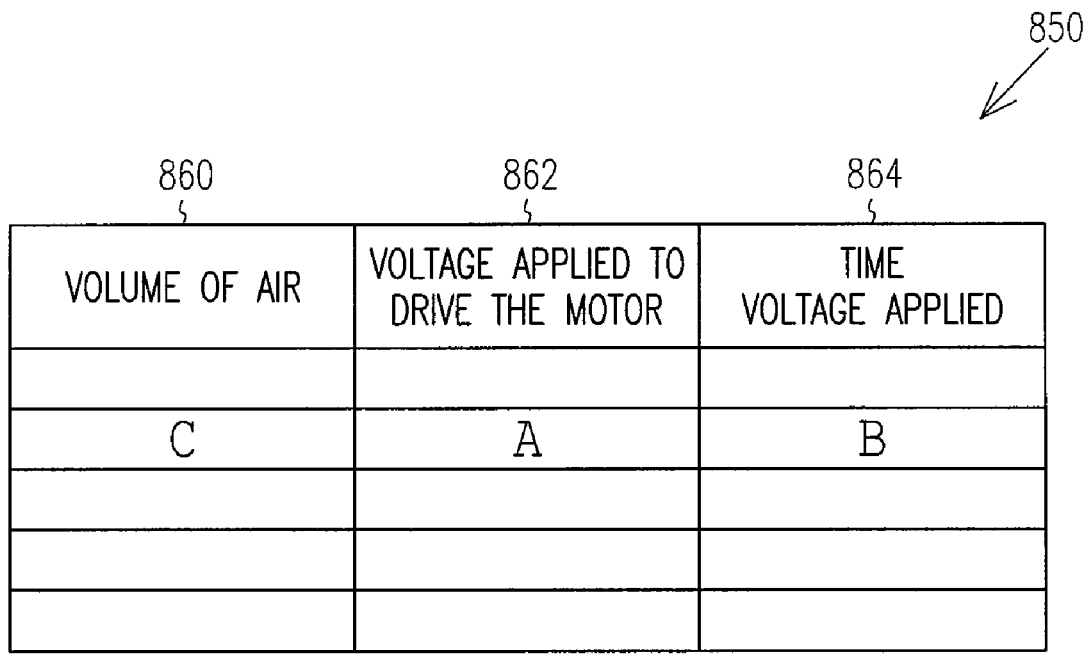
FIG. 8B illustrates a look up table for use in controlling the motor of a collection module, according to another example embodiment.
Figure 9:
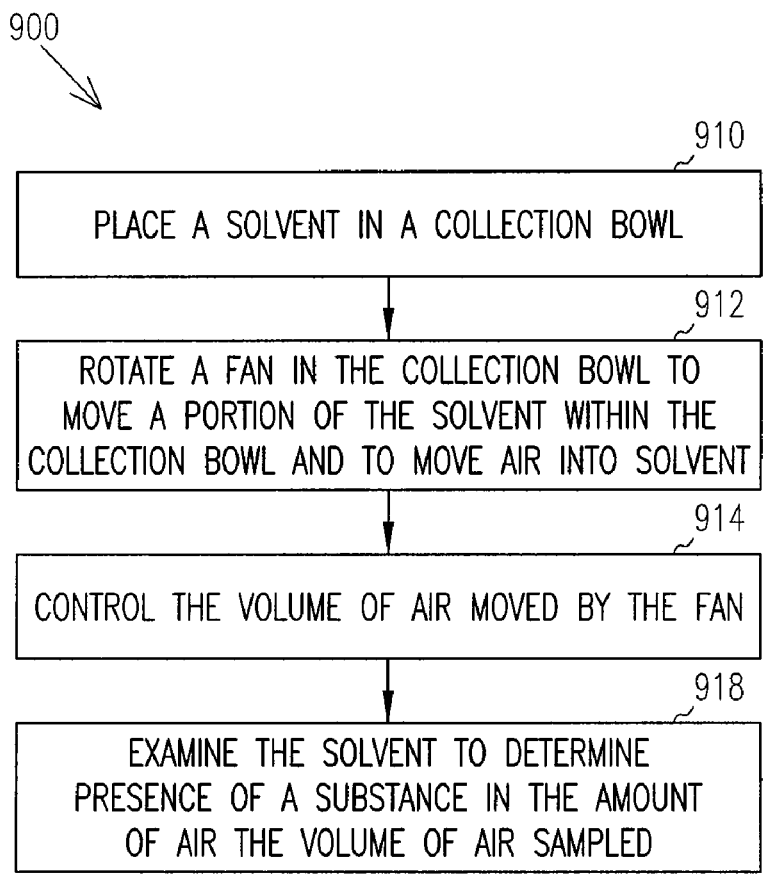
FIG. 9 is a flow diagram of an air sampling method, according to an example embodiment.

FIG. 8B illustrates a lookup table 850 for use in controlling the motor 240 of a collection module, such as collection module 200 or collection module 600, according to an example embodiment. In this example embodiment, an open loop control is used. More specifically, the volume of air or sample size 810 is determined by measuring the volume output from a fan in terms of voltage applied to the motor for a selected amount of time. Therefore, the table lookup 850 relates a sample size or volume of gas or air 860 to the voltage 862 applied the motor 240 for a selected amount of time 864. Therefore, in an open loop control embodiment of this example, there would be no sensor either on the inlet or outlet of the collection module. The motor 240 would simply be driven at a selected voltage 862 for a selected amount of time 864 to produce a volume of air 860. For example, using lookup table 850 the motor 240 would be driven with a voltage A, for B units of time to produce a volume of air C. In this way the volume of air or sample size could be approximated or determined without the need for an extra sensor or an extra tool for measuring the volume or pressure differential or other parameter of the gas or air passing through a collection module.

A method 900 for collecting air samples includes placing a solvent in a collection bowl 910, rotating a fan in the collection bowl to move a portion of the solvent within the collection bowl and to move air into solvent 912, and controlling the amount of air moved by the fan 914. Controlling the amount of air moved by the fan 914 can use a feedback control apparatus, or an open loop control apparatus. The method 900 also includes examining the solvent to determine presence of a substance in the amount of air 918.

Figure 10:
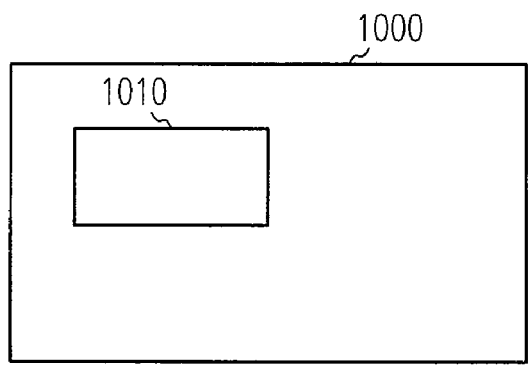
FIG. 10 is a block diagram of a computer readable medium according to an example embodiment.

FIG. 10 is a block diagram of a computer readable medium 1000 according to an example embodiment. The computer program product for use with a computer system associated with an air or gas sampling device 100 includes a computer usable medium 1000 having a set of instructions 1010 executable by a suitably programmed information handling system embodied in the computer usable medium. The computer usable medium 1000 can be any sort of medium including a floppy disk, a connection to the internet, a connection to a local area network, a connection to a wide area network or the like. The connection can be either a wire or hardware connection, a radio frequency connection or a infrared connection. The set of instructions 1010 causes the computer system to control the flow of the gas through the air or gas sampling device 100. The set of instructions will direct the microprocessor to the memory 132, 632 (shown in FIGS. 1 and 6) locations corresponding to a table look up 800 (shown in FIG. 8) during flow control operations. The instructions also include instructions related to controlling the air or gas flow through a collection module. In some embodiments, the instructions associated with the computer useable medium 1000 can also include taking samples at set times or on a periodic basis. In other embodiments, the instructions associated with the computer useable medium 1000 can also include taking of samples at random times.

A sampling system includes a collection module including a gas handler, and a flow controller in communication with the gas handler of the collection module. The flow controller controls the gas handler to move a selected volume of gas through the collection module. The collection module also includes a collection bowl. The gas handler is positioned proximate the collection bowl. The collection bowl has an opening therein. A tubular gas inlet passes through the opening. The tubular gas inlet includes a first end terminating outside of the collection bowl, and a second end terminating inside of the collection bowl. The second end terminates between the top and bottom of the collection bowl. A portion of the gas handler is positioned about the circumference of the second end of the tubular gas inlet. The gas handler is positioned to direct a portion of the gas passing through the tubular inlet toward a surface of the collection bowl. The collection bowl and tubular gas inlet are joined to allow the collection bowl to hold a liquid. In some embodiments, the collection bowl includes a concave surface. In still other embodiments, a frame is attached the collection bowl, the gas mover attached to the frame. In some embodiments, the gas mover includes a squirrel cage and the flow controller includes a feedback control loop. In some example embodiments, the sampling system includes a microprocessor, and a memory in communication with the microprocessor, and a lookup table stored within the memory. The microprocessor refers to the lookup table to control the gas mover.

A sampling system includes a collection module. The collection module also includes a concave collector bowl having an air inlet terminating within the collector bowl, a frame attached to the collector bowl, a motor attached to the frame, and a squirrel cage fan coupled to the motor. The squirrel cage fan is positioned within the collector bowl near the one end of the air inlet terminating within the bowl. The sampling system also includes a flow controller in communication with the motor. The flow controller controls the motor and attached squirrel cage fan to move a selected volume of gas through the collection module. In some embodiments, the flow controller includes a microprocessor. The microprocessor including an instruction set for controlling the motor and attached squirrel cage fan. A memory unit is in communication with the microprocessor. The memory unit includes a lookup table relating a volume of gas moved by the squirrel cage fan to the revolutions per minute of the squirrel cage fan. In other embodiments, the sampling system includes a gas volume measurement device, and the flow controller employs a feedback control system for controlling the motor and attached squirrel cage fan in response to an input from the gas volume measurement device. In one example embodiment, the gas volume measurement device includes an impeller positioned in a gas outlet of the sampling system. In another example embodiment, the sampling system includes a differential pressure sensor, and the flow controller employs a feedback control system for controlling the motor and attached squirrel cage fan in response to an input from the differential pressure sensor.

The foregoing description of the specific embodiments reveals the general nature of the invention sufficiently that others can, by applying current knowledge, readily modify and/or adapt it for various applications without departing from the generic concept, and therefore such adaptations and modifications are intended to be comprehended within the meaning and range of equivalents of the disclosed embodiments.

It is to be understood that the phraseology or terminology employed herein is for the purpose of description and not of limitation. Accordingly, the invention is intended to embrace all such alternatives, modifications, equivalents and variations as fall within the spirit and broad scope of the appended claims.

What is claimed is:

1. A method for collecting air samples comprising: placing a solvent in a collection bowl; rotating a fan in the collection bowl to move a portion of the solvent within the collection bowl and to move air into solvent, wherein the solvent does not contact blades of the fan to move the portion of the solvent or to move air into the solvent; sensing the amount of air being moved by the fan; and controlling the amount of air moved by the fan.

2. The method of claim 1 further wherein controlling the amount of air moved by the fan uses a feedback control apparatus.

3. The method of claim 1 further wherein controlling the amount of air moved by the fan uses an open loop control apparatus.

4. The method of claim 1 further comprising examining the solvent to determine presence of a substance in the amount of air.

* * * * *